United States Patent [19]
Djuric et al.

[11] Patent Number: 4,895,869
[45] Date of Patent: Jan. 23, 1990

[54] PHENYLENE, FURYL, AND THIENYL LEUKOTRIENE B₄ ANALOGUES

[75] Inventors: Stevan W. Djuric, Glenview; Richard A. Haack, Chicago; Julie M. Miyashiro, Evanston, all of Ill.

[73] Assignee: C. D. Searle & Co., Chicago, Ill.

[21] Appl. No.: 202,279

[22] Filed: Jun. 3, 1988

[51] Int. Cl.⁴ ..................... A61K 3/38; C07D 333/22
[52] U.S. Cl. ........................................ 514/438; 549/79
[58] Field of Search ................... 549/77, 79, 496, 501; 514/438

[56] References Cited

U.S. PATENT DOCUMENTS 4,546,194  10/1985  Miyano .
4,791,133  12/1988  Djuric et al. ..................... 514/438

OTHER PUBLICATIONS

Furber et al., J. Chem. Soc. Perkins-Trans I, (7): 1573–78 (1987).
Biochem and Biopys. Res. Comm., 138, 540–546 (1986).
Lewis, et al., J. Clin. Inves., 73, 889–897 (1984).
Bray, Brit. Medical Bull., 39, 249–254 (1983).

Primary Examiner—Alan Siegel
Attorney, Agent, or Firm—M. J. Kanady; P. D. Matukaitis; R. A. Williams

[57] ABSTRACT

This invention related to leukotriene B₄ antagonists having the structure

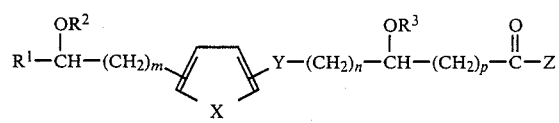

and the pharmaceutically acceptable addition salts thereof;

wherein $R^1$ is lower alkyl having 1–10 carbon atoms; or lower alkenyl or alkynyl having 2–10 carbon atoms; or lower alkadienyl having 3–10 carbon atoms; or lower alkadienyl or alkenynyl having 4–10 carbon atoms;

wherein $R^2$ and $R^3$ are the same or different and represent hydrogen or lower alkyl having 1–6 carbon atoms;

wherein X is CH=CH, S, or O;

wherein Y is CH=CH or C≡C;

wherein Z is $OR^4$ or $NR^5R^6$, and wherein $R^4$ represents H, lower alkyl having 1–6 carbon atoms, or a pharmaceutically acceptable cation, and wherein $R^5$ and $R^6$ act independently and represent H or lower alkyl having 1–6 carbon atoms, or $R^5$ and $R^6$ may act together with N to form a cycloamine of the formula:

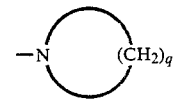

wherein q is an integer from 2–5;
wherein m and n are the same or different and either 1 or 0; and
wherein p is an integer from 1 to 5.

3 Claims, No Drawings

PHENYLENE, FURYL, AND THIENYL LEUKOTRIENE B4 ANALOGUES

BACKGROUND OF THE INVENTION (a) Field of the Invention

The present invention relates to pharmaceutical agents (compounds) which act as leukotriene B$_4$ (LTB$_4$) antagonists in mammals. The compounds of the present invention are useful in treating inflammatory conditions in mammals such as psoriasis, Crohn's disease, ulcerative colitis and the like.

(b) Prior Art

LTB$_4$ (Formula I) is an arachidonic acid metabolite which is an important mediator of inflammation in mammals. As a mediator of inflammation LTB$_4$ is known to induce chemotaxis, chemokinesis aggregation, and degranulation of leukocytes in vitro. and to induce accumulation of polymorphonuclear leukocytes, and increase vascular permeability and edema formation in vivo.

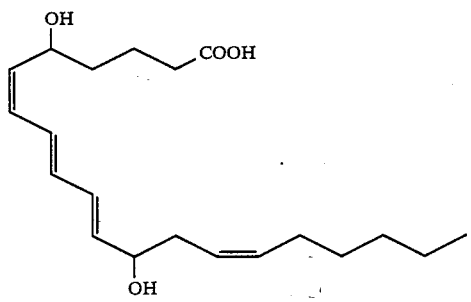

I

Particularly high levels of LTB$_4$ are detected in lesions in inflammatory diseases such as rheumatoid or spondylarthritis, gout, psoriasis, ulcerative colitis, Crohn's disease, and some respiratory diseases.

Accordingly, it is an object of this invention to produce compounds for use as pharmaceutical agents which will exhibit LTB$_4$ antagonist activity in mammals.

A potential LTB$_4$ antagonist (Formula II), which is structurally different from the compounds of the present invention, is disclosed in Biochem. and Biophys. Res. Comm., 138 540-546 (1986).

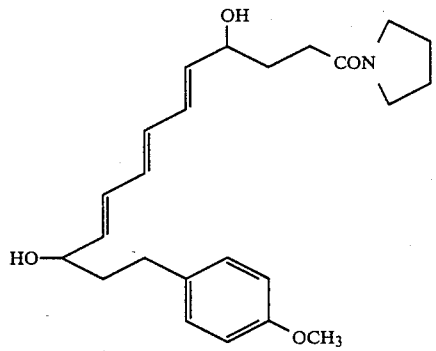

II

In this article, the authors also suggest that they have found antagonistic activity in a series of unidentified unsaturated dihydroxy fatty acid derivatives which are to be the subject of a future publication.

The pharmacology of the biologically active leukotrienes is generally discussed in J. Clin. Invest. 73, 889.897 (1984).

SUMMARY OF THE INVENTION

This invention encompasses compounds of the formula

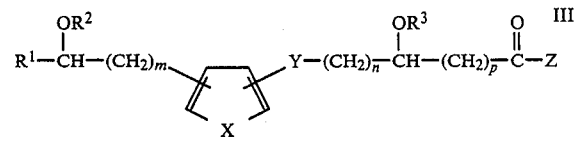

III and the pharmaceutically acceptable non toxic addition salts thereof;

wherein R$^1$ is lower alkyl having 1–10 carbon atoms; lower alkenyl having 2–10 carbon atoms; lower alkynyl and having 2–10 carbon atoms; lower alkadienyl having 3–10 carbon atoms; lower alkadiynyl having 4–10 carbon atoms; or alkenynyl having 4–10 carbon atoms;

wherein R$^2$ and R$^3$ are the same or different and represent hydrogen or lower alkyl having 1–6 carbon atoms;

wherein X is CH=CH, S, or O;

wherein Y is CH=CH or C≡C;

wherein Z is OR$^4$ or NR$^5$R$^6$, and wherein R$^4$ represents H, lower alkyl having 1–6 carbon atoms, or a pharmaceutically acceptable cation, and wherein R$^5$ and R$^6$ act independently and represent H or lower alkyl 1–6 carbon atoms, or R$^5$ and R$^6$ may act together with N to form a cycloamine of the formula:

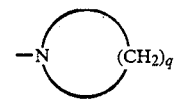

IV wherein q is an integer from 2–5;

wherein m and n are the same or different and either 1 or 0; and wherein p is an integer from 1 to 5.

DETAILED DESCRIPTION

This invention encompasses compounds of Formula III as previously described including any stereoisomers thereof. A particularly preferred embodiment of the present invention is encompassed by a compound of the formula:

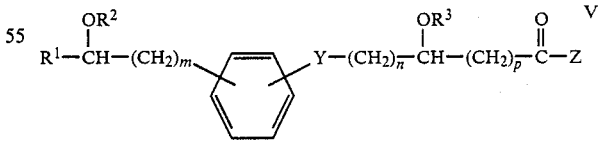

V wherein R$^1$, R$^2$, R$^3$, Y, Z, R$^4$, R$^5$, R$^6$, m, n, p, and q are as previously defined for Formulas III and IV.

The term "alkyl" as used to described R$^1$, R$^2$, R$^3$, R$^4$, R$^5$, and R$^6$ means straight or branched chain alkyls having 1–10 carbon atoms.

The term "alkenyl" as used to describe R$^1$ means straight or branched chain alkenyls having 2–10 carbon atoms.

The term "alkynyl" as used to describe $R^1$ means straight or branched chain alkynyls having 2-10 carbon atoms.

The term "alkadienyl" as used to describe $R^1$ means straight or branched chain alkadienes, including allenes, having 3-10 carbon atoms.

The term "alkadiynyl" as used to describe $R^1$ means straight or branched chain alkadiynyls having 4-10 carbon atoms.

The term "alkenynyl" as used to describe $R^1$ means straight or branched chain alkenynyls having 4-10 carbon atoms.

The term "pharmaceutically acceptable cations" as used to describe $R^4$ refers to cations such as ammonium, sodium, potassium, lithium, calcium, magnesium, ferrous, zinc, copper, manganous, aluminum, ferric manganic, ammonium, tetraalkyl-ammonium and the like.

The term "pharmaceutically acceptable non toxic addition salts" refers either to those base derived salts of any compound herein having a carboxylic acid function.

The base derived salts may be derived from pharmaceutically acceptable non toxic inorganic or organic bases. Among the inorganic bases employed to produce said pharmaceutically acceptable salts are the hydroxide bases of the "pharmaceutically acceptable cations" disclosed above.

Among the organic bases employed to produce said pharmaceutically acceptable salts are the pharmaceutically acceptable non toxic bases of primary, secondary, and tertiary amines. Especially preferred non toxic bases are isopropylamine, diethylamine, ethanolamine, dicyclohexylamine, choline, and caffeine.

All the pharmaceutically acceptable non-toxic addition salts are prepared by conventional processes well known to those of ordinary skill in the art.

The compounds of this invention are generally prepared by separately adding two chains to an appropriately substituted aromatic moiety. The first chain can be added by initially performing a nucleophilic addition of a bromoalk-l-yne compound, such as via a Grignard reaction to a bromo-substituted aromatic aldehyde. The aromatic moiety can be phenyl, thienyl or furyl. The Grignard reagent adds to the aldehyde group to form an alkynol compound. The resulting hydroxyl group is typically protected by reaction with a trialkylchlorosilane, preferably t-butyldimethylchlorosilane.

The length of the alkyne side chain can be optionally increased to produce an $R^1$ of the desired length. One method of increasing the chain length is to convert the terminal acetylene into an anion by reaction with an alkyl lithium compound in an aprotic solvent. This anion can then be added to a straight or branched chain alkyl iodide via a nucleophilic substitution. By varying the chain lengths of the bromoalkyne and the iodide compound in the above reaction, the necessary variations can be achieved to produce the $R^1$ substituents claimed in this invention.

The second chain can be added to the above aromatic moiety via a catalytic reaction. By selecting a hydroxyester containing a terminal triple bond and by protecting the hydroxyl group with a trialkylsilane, preferably t-butyldimethylchlorosilane, one can substitute the terminal acetylene for the bromo on the aromatic moiety. By varying the chain length and the position of the hydroxyl group, one can achieve the necessary variations to produce diyne compounds encompassed by the present invention.

The diyne compounds can be catalytically hydrogenated over Lindlar catalyst to produce diene compounds also encompassed by the present invention.

The biological activity possessed by the compounds of this invention was indicated by positive results to the "$LTB_4$ Receptor Binding Assay" and the "Human Neutrophil Degranulation Assay".

Preparation of Human Neutrophils

For use in both the "$LTB_4$ receptor Binding Assay" and the "human Neutrophil Degranulation Assay", neutrophils were purified from venous blood of normal human donors using standard techniques of dextran sedimentation, centrifugation on Histopaque ® (density solution) and hypotonic lysis of erythrocytes (Boyum, A., *Isolation of Leukocytes From Human Blood: Further Observations.* Scand. J. Lab. Clin. Inves. 21 (Suppl. 97): 31, 1968). The purity of isolated neutrophils was $\geq 95\%$.

$LTB_4$ Receptor Binding Assay

Neutrophils ($4-6\times 10^6$) in 1 ml of Hanks balanced salt solution containing 10 mM Hepes Buffer (HBSS), pH 7.4 and 30 $\mu$M nordihydroguaiaretic acid were incubated with 0.6 nM ($^3$H) $LTB_4$ in the presence or absence of test compounds. The incubation was carried out at 0° C. for 45 minutes and terminated by adding 5 ml of ice cold HBSS followed by rapid filtration of incubation mixture under vacuum through GF/C glass fiber filters. The filters were further washed with 10 ml HBSS and their radioactivity was determined. Specific binding was defined as the difference between total binding and nonspecific binding which was not displaced by $10^{-7}$M unlabeled $LTB_4$.

The inhibition of specific binding was determined for representatives compounds of this invention, and the corresponding $IC_{50}$ values calculated (Table 1). An $IC_{50}$ is the concentration of the compound of interest which will inhibit the binding of $LTB_4$ by 50% of the $LTB_4$ receptors. For example, for the compound of Example 7, the $IC_{50}$ was determined to be approximately Human Neutrophil Degranulation Assay $LTB_4$ induced neutrophil degranulation was determined by measuring the release of myeloperoxidase activity into the incubation medium. Neutrophils ($3\times 10^6$) in 1 ml HBSS solution were preincubated with cytochalasin B(5 $\mu$g) at 37° C. for 5 minutes, followed by preincubation with test compounds for 7 minutes. Neutrophilsere then incubated for 2 to 20 minutes with either $LTB_4$(5 $\times 10^{-8}$M) or the chemotactic peptide f-met-leu-phe ($5\times 10^{-6}$M) to induce degranulation. Following incubation, samples were centrifuged and myleoperoxidase was extracted from the cell pellets by sonication in phosphate buffer containing 0.4% Triton X-100. Triton X-100 was also added to the supernatents to a concentration of 0.4%. The supernatants and the pellet extracts were then assayed spectrophotometrically for myeloperoxide activity by determining the rate of decomposition of $H_2O_2$ with o-dianisidine as hydrogen donor as described by Renlund D. G., MacFarlane J. L., Christensen, R. D., Lynch R. E., and Rothstein, G., *A Quantitative And Sensitive Method For Measurement Of Mveloperoxidase,* Clinical Research 28:75A, 1980). Myeloperoxidase activity released into the supernatant was expressed as the percent of the average total activity (pellet plus supernatant).

The inhibition of LTB$_4$ induced neutrophil degranulation was determined for representative compounds of this invention and their corresponding IC$_{50}$ values were calculated (Table 1). The concentration of a compound which inhibited LTB$_4$ induced neutrophil degranulation by 50% was determined to be its IC$_{50}$ value.

By virtue of their activity as LTB$_4$ antagonists, the compounds of Formula I are useful in treating inflammatory conditions in mammals such as psoriasis, Crohn's disease, ulcerative colitis and the like. A physician or veterinarian of ordinary skill can readily determine whether a subject exhibits the inflammatory condition. The preferred utility relates to treatment of ulcerative colitis.

The compounds of the present invention can be administered in such oral dosage forms as tablets, capsules, softgels, pills, powders, granules, elixirs, or syrups. The compounds may also be administered intravascularly, intraperitoneally, subcutaneously, intramuscularly, or topically using forms known to the pharmaceutical art. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, a therapeutically effective amount of one or more compounds of the present invention may be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof. For oral administration in liquid forms, such as in softgels, elixirs, syrups, drops and the like, a therapeutically effective amount of the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes or combinations thereof. Lubricants for use in these dosage forms include boric acid, sodium benzoate, sodium acetate, sodium chloride, and the like or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, one or more compounds of the present invention may be combined with a suitable carrier such as water, saline, aqueous dextrose, and the like. For topical administration, such as for psoriasis, therapeutically effective amounts of one or more compounds of the present invention can be combined with pharmaceutically acceptable creams, oils, waxes, gels and the like. Regardless of the route of administration selected, the compounds of the present invention are formulated into pharmaceutically acceptable dosage forms by conventional methods known to those skilled in the art. The compounds may also be formulated using pharmacologically acceptable base addition salts. Moreover the compounds or their salts may be used in a suitable hydrated form.

Regardless of the route of administration selected, a non toxic but therapeutically effective quantity of one or more compounds of this invention is employed in any treatment. The dosage regimen for preventing or treating inflammatory conditions with the compounds of this invention is selected in accordance with a variety of factors, including the type, age, weight, sex, and medical condition of the patient, the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employe relatively low doses at first and subsequently increase the dose until a maximum response is obtained. Daily dosages of the compounds of the invention are ordinarily in the range of about 1.0 mg/kg up to about 21.0 mg/kg, [preferably in the range of about 200 to 14.0 mg/kg (orally)].

The following examples illustrate the methods used to prepare the compounds of this invention. These examples are given by way of illustration only and in no way should be construed as limiting the invention in spirit or in scope, as many modifications in materials and methods will be apparent from this disclosure to those skilled in the art.

In the following examples, and throughout this application a wavey line ($\sim$) defines a substituent as having optional R or S stereochemistry. A broken triangular shaped line (⫼) defines the substituent at the base of the triangle as coming out of the plane of the paper, whereas a substituent at the apex of the broken triangle, is defined as going into the plane of the paper.

TABLE 1
Biological Activity For Representative Compounds Of The Invention
| Compound (Example No.) | Structure | Inhibition of Receptor Binding of LTB$_4$ IC$_{50}$(μM) | Inhibition of LTB$_4$ Induced Neutrophil Degranulation IC$_{50}$(μM) |
|---|---|---|---|
| 7 | 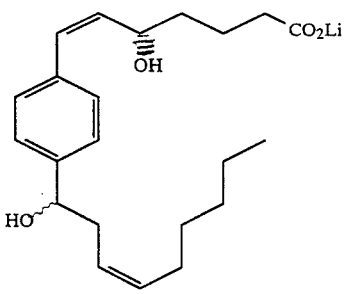 | 5 | 0.7 |
| 11 | 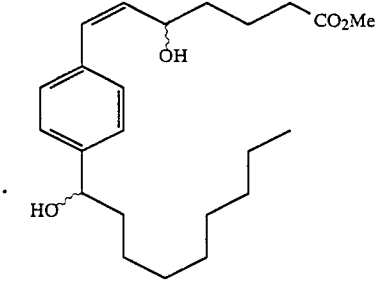 | 1 | 0.65 |
| 21 | 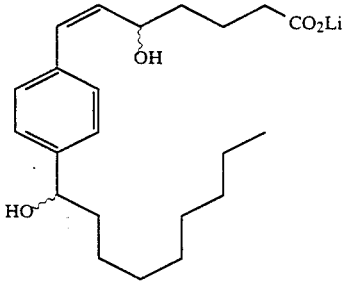 | 2 | 1.0 |
| 22 | 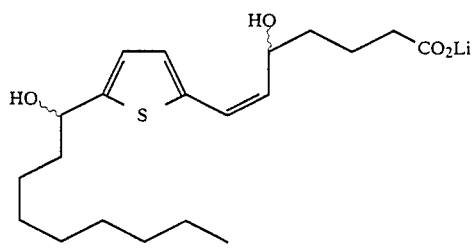 | 5 | 1.8 |
| 23 | 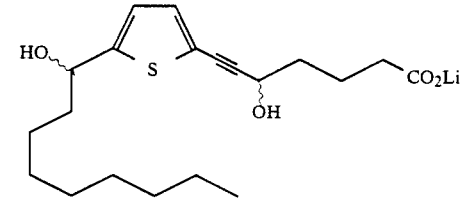 | 20% inhibition at 10 μM | 8.7 |

DESCRIPTION OF THE PREFERRED EMBODIMENT

EXAMPLE 1

1-(p-bromophenyl)-but-3-yn-1-ol

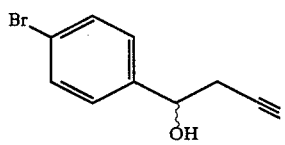

To 4.1 g of flame dried Mg was added 50 ml of diethyl ether ("ether") followed by the addition of a few iodine crystals. To this was added a 10 ml aliquot of a solution containing 15ml (168.9 mmol) of propargyl bromide in 50 ml of ether. The reaction was started by the addition of 25 mg of $HgCl_2$. The remaining solution of propargyl bromide in ether was then added at a rate sufficient to maintain a steady reflux. Once addition was complete, the mixture was stirred 1 hour at room temperature (R.T.) and then placed in an ice bath and cooled to 0° C. To the cooled reaction mixture was added dropwise with stirring over a 1 hour period, a solution containing 25 g (135.1 mmol) of 4-bromobenzaldehyde dissolved in 30 ml of ether and 30 ml of THF. Once addition was complete, the ice bath was removed and the reaction mixture stirred overnight at room temperature (R.T.). The reaction was quenched with a saturated $NH_4Cl$ solution. The layers were separated and the aqueous layer was extracted twice with ether. The combined extracts were washed 1× each with $H_2O$, and brine and then dried ($MgSO_4$). Removal of the solvent produced 30.2 g of a crude yellow oil which was semi-purified by high pressure liquid chromatography, HPLC, (silica; gradient elution with methyl t-butyl ether hexane) to yield 20.8 g of a reaction mixture that was 80% pure in the titled product.

EXAMPLE 2

1-(p-bromophenyl)-1-(t-butyldimethylsiloxy)-3-butyne

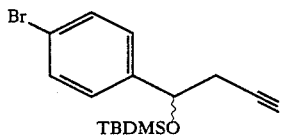

TBDMSO = t-butyldimethylsiloxy

A solution containing 19 g (84.5 mmol) of the semi purified reaction product of Example 1 dissolved in 50 ml of DMF was cooled to 0° C (ice bath) and 12.9 g (190 mmol) of imidazole was added in one portion. The reaction mixture was stirred 10 minutes until all the imidazole dissolved and then was added in one portion 14.3 g (95 mmol) of t-butyldimethylchlorosilane. After stirring for 5 minutes, the ice bath was removed and the reaction mixture was stirred for an additional 2 hrs. at R.T. The reaction was then poured into 500 ml of ether and washed 3× with 50 cc of $H_2O$ and 1× with 100 ml of brine. The organic layer was then separated, dried ($MgSO_4$), and removal of all solvent yielded 29.32 g of crude product. Separation by reverse phase HPLC (gradient elution with acetonitrile water) yielded 9.1 g of the titled product.

Analysis for $C_{16}H_{23}OSiBr$ (MW=339.35):

Calcd: C, 56.63; H, 6.83; Br, 23.55.
Found: C, 56.61; H, 6.88; Br, 23.56.

EXAMPLE 3

1-(p-bromophenyl)-1-(t-butyldimethylsiloxy)-3-nonyne

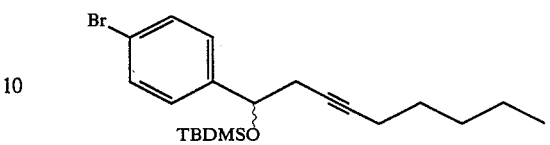

TBDMSO = t-butyldimethylsiloxy

To 2.2 g (63 mmol) of the silylacetylene of Example 2 dissolved in 50 ml of dry THF and cooled to −78° C. under argon was added dropwise 5.6 ml (7.0 mmol) of a 1.25 M solution of methyl lithium in diethyl ether. Upon addition, the reaction was warmed to −10° C. and stirred at −10° C. for 30 min. Iodopentane (1.2 ml, 9.0 mmol) was then added followed by 5.0 ml of hexamethylphosphoric triamide (HMPA) whereupon the reaction mixture was warmed to R.T. and stirred overnight. The reaction was quenched with about 5.0 ml of $H_2O$, then poured into hexane and washed 4× with $H_2O$, and 1x with brine. The organic layer was dried ($MgSO_4$) and the solvent removed to yield a dark red oil which was purified by medium pressure liquid chromatography (MPLC) eluting with hexane to yield 2.14 g of the titled product as a pale yellow oil.

$^1$H N.M.R $\delta_{TMS}$ $CDCl_3$ (300 MHz):
−0.08(s,3H); 0.03(s,3H); 0.9(s&t, 12H); 1.3(br.m,4H); 1.43(br.m,2H); 2.1(tt,2H); 2.45(m,2H); 4.72(t,$^1$H); 7.32(dd, 4H).

EXAMPLE 4

Methyl 7-[4-[1-(t-butyldimethylsiloxy)-3-nonynyl]phenyl]-5S-(t-butyldimethylsiloxy)-6-heptynoate

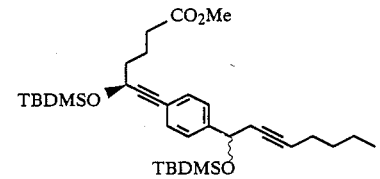

The following reagents were added to a pressure vessel: 0.1 g (0.24 mmol) of 2-(t-butyldimethylsiloxy)-1-p-bromophenyl-3-nonyne, 0.065 g (0.24 mmol) of methyl 5S-(t-butyldimethylsiloxy)-6-heptynoate prepared according to the procedure of Nicolaou et al., J.A.C.S., 106, 2748 (1984) employing the optically active 5S-alcohol, 1 ml of piperidine, and 6 mg (0.005 mole, 2 mole %) of $Pd(PPh_3)_4$. The vessel was degassed with arqon, sealed and the reaction mixture was then heated at 100–120° C. for 2 hrs. with stirring. The reaction was then cooled to room temperature, diluted with diethyl ether, filtered, and stripped of all solvent. The residue was purified by MPLC, eluting with 2.5% ethyl acetate-hexane to yield 0.7g of the titled product.

$^1$H N.M.R. $\delta_{TMS}$ $CDCl_3$ (300 MHz):
−0.08(s, 3H); 0.04(s, 3H); 0.15(s, 3H); 0.17(s, 3H); 0.88(s&t, 12H); 0.92(s, 9H); 1.29(m, 4H); 1.43(m, 2H); 1.79(m, 4H); 2.09(tt, 2H); 2.35–2.6(complex, 4H); 3.66(s, 3H); 4.59(t, $^1$H); 4.74(t, $^1$H); 7.3(dd, 4H).

EXAMPLE 5

Methyl 7-[4-[1-(t-butyldimethylsiloxy)-3Z-nonenyl]phenyl]-5S-(t-butyldimethylsilkoxy)-6Z-heptenoate

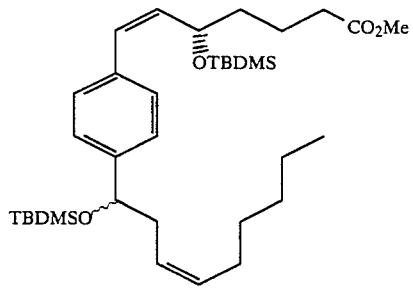

To 0.07 g of the titled product of Example 4 in 10 ml of hexane was added 0.1 ml of quinoline and 10 mg of Lindlar catalyst. The mixture was stirred under a H$_2$ atmosphere for 7 hours at room temperature. The reaction was recharged with an additional 10 mg of catalyst and the reaction was permitted to run overnight. The reaction mixture was filtered through Celite ® (diatomaceous earth) and the filtrate was evaporated to give an oil. Purification by MPLC eluting with 2.5% ethyl acetate hexane produced 0.060 g of the titled product.

$^1$H N.M.R. $\delta_{TMS}$ CDCl$_3$ (300 MHz):

−0.15(s, 3H); 0.1(s, 3H); 0.02(s, 3H);

0.05(s, 3H); 0.85(s, 9H); 0.9(s&t, 12H);

1.28(br.m, 4H); 1.55 1.9(br.m, 6H); 1.96(m, 2H);

2.34–2.6(br.m&t, 4H); 3.7(s, 3H); 4.65(m, 2H);

5.40(m, 2H); 5.65(dd $^1$H); 6.44(d, $^1$H); 7.2(dd, 4H).

EXAMPLE 6

Mixture of methyl 7-[4-(1-hydroxy-3Z-nonenyl)phenyl]5S-hydroxy-6Z-heptenoate and

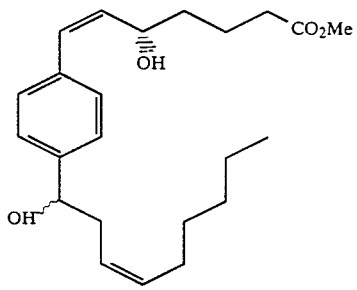

(A)

Tetrahydro-6S-[2-[4-(1-hydroxy-3Z-nonenyl)phenyl]-Z-ethyleneyl]-2H-pyran-2-one (B)

To 0.32 g (0.53 mmol) of the product of Example 5 dissolved in 0.5 ml of DMF was added 6.4 mg (2.1 eq.) of KF, 1.4 mg (0.1 eq.) of 18-crown-6-polyether, and 2 μl (2.1 eq.) of H$_2$O. The reaction was stirred under Ar for 24 hrs. An additional 6 mg of KF was then added and the reaction was stirred overnight at R.T. The reaction mixture was then poured into water and the aqueous solution extracted 3× with ether. The combined extracts were washed 2x with H$_2$O and 2x with brine and dried (MgSO$_4$). Removal of the solvent in vacuo produced an oil. The oil was purified by flash chromatography (silica, gradient elution with ether—petroleum ether).

Fraction I contained 0.00247 g (0.0066 mmol) of the ester (A). Fraction II contained 0.00166 g (0.0049 mmol) of the lactone (B). Fraction III contained an additional 0.00609 g of the ester and lactone in a 1:4 ratio (determined by $^1$H N.M R.)

Lactone $^1$H N.M.R. $\delta_{TMS}$ CDCl$_3$ (300 MHz):
0.88(t, 3H); 1.27(m, 6H); 1.7 −2.1(complex, 5H);
2.4–2.7(complex, 4H); 4.63(t, 1H); 5.16(m, 1H);
5.3–5.65(m, 2H); 5.22(dd, 1H); 6.2(d, 1H);
7.33(dd, 4H).

Ester:

$^1$H N.M.R. $\delta_{TMS}$ CDCl$_3$ (300 MHz):
0.89(t, 3H); 1.25(m, 6H); 1.6–1.8(m, 4H);
2.02(m, 2H); 2.35(t, 2H); 2.4–2.64(m, 4H);
3.68(s, 3H); 4.58(m, 1H); 4.71(t, 1H);
5.4(m, 1H); 5.58(m, 1H); 5.66(dd, 1H);
6.55(d, 1H); 7.3(dd, 4H).

EXAMPLE 7

7[4-(1-hydroxy-3Z-nonenyl)phenyl]-5S-hydroxy 6Z-heptenoic acid, lithium salt

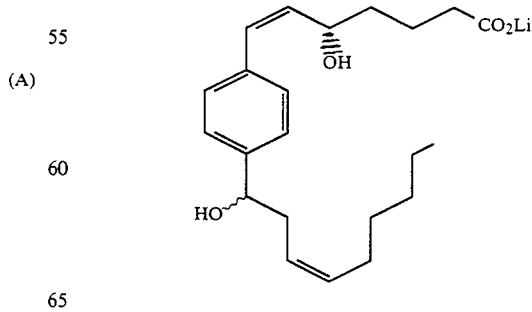

The combined ester and lactone products (0.017 mmol) of Example 6 were dissolved in 0.3 ml of methanol and cooled to 0° C. Upon dissolution, 0.1 ml of H$_2$O was added followed by 20 μl (0.02 mmol) of a 1M LiOH solution. The slurry was stirred for five minutes and then warmed to room temperature. After 24 hrs, an additional 5 μl of 1M LiOH was added and stirring continued for an additional 24 hours. The reaction mixture was then evaporated to dryness under a stream of N₂ and the last traces of solvent were removed under high vacuum. The reaction produced 6.2 mg of the titled product.

$^1$H N.M.R. $\delta_{d4\ Na\text{-}TSP}$ D₂O (300 MHz):
5.2–5.5(m, 2H); 5.63(dd, 1H); 6.07(d, 1H); 7.3(dd, 4H).

EXAMPLE 8

Methyl 7-[4-(1-hydroxy-3-nonynyl)phenyl]-5S-hydroxy-6-heptynoate

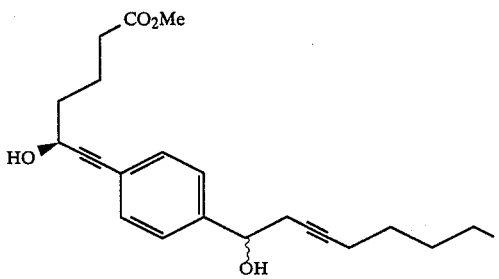

To 0.044 g (0.074 mmol) of the product of Example 4 was added to 0.3 ml (0.3 mmol) of 1M tetra-n-butylammonium fluoride in tetrahydrofuran (THF) with stirring at room temperature. The reaction mixture was stirred 6 hours at room temperature and then poured into brine. The brine, containing the reaction mixture, was then extracted 5× with diethyl ether and dried (MgSO₄). The dried reaction mixture was then stripped of all solvent and the residue and taken up in 10 ml of methanol. To the methanol solution was added 2 mg of sodium methoxide and the reaction was stirred overnight. The reaction was stripped in vacuo to qive an oil. The oil was purified by flash chromatography (silica; gradient elution with ether petroleum ether) to give 5 mg of the titled product.

$^1$H N.M.R. $\delta_{TMS}$ CDCl₃ (300 MHz):
0.9(t, 3H); 1.3(m, 4H); 1.48(m, 2H);
1.65(broad s, 1H); 1.85(m, 4H); 2.15(m, 3H);
2.42(t, 2H); 2.5–2.65(m, 2H); 3.59(s, 3H);
4.61(broad s, 1H); 4.8(t, 1H); 7.87(dd, 4H).

EXAMPLE 9

7-[4-(1-hydroxyl-3-nonynyl)phenyl]-5S-hydroxy-6-heptynoic acid, lithium salt

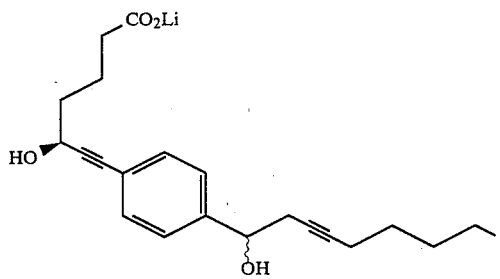

The titled product was prepared according to the reaction described in Example 7, employing 5 mg (.0135 mmol) of the product of Example 8 instead of the product of Example 6. The reaction was run until thin layer chromatography (TLC) indicated that al starting material was consumed. The yield was 4.9 mg of titled material.

EXAMPLE 10

1-(p-bromophenyl)-1-nonanol

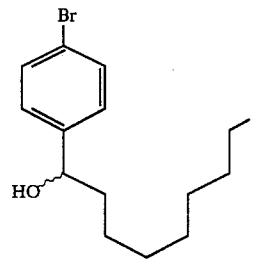

In a 100 ml round bottom flask with a Y adapter, condensor, and a 10 ml addition funnel was added 0.38 g (15.63 mmol) of Mg turnings which had been ground with a mortar and pestle. The apparatus was then flushed with argon and flame dried. After allowing the apparatus to cool under arqon, 4 ml of anhydrous diethyl either was added to the Mg. While vigorously stirring the Mg in the ether, 2.52 g (13.05 mmol) of 1-bromooctane in 3 ml of diethyl ether was added dropwise. After 5 drops, the Grignard reaction started and the addition was continued at a rate sufficient to maintain a steady reflux. After addition was complete, 4 ml of dry THF was added to the Grignard reagent and it was stirred at R.T. for an additional ½ hour. A warm water bath was then placed under the flask, and refluxing was continued for 15 minutes. Afterwards, the reaction was cooled to 0° C. with an ice bath and 2.00 g (16.81 mmol) of p bromobenzaldehyde in 4 ml of the THF was added. The reaction was stirred at R.T. for 1.5 hrs., whereupon the Grignard was quenched with saturated NH₄Cl. The organic layer was washed with H₂O and brine, then dried (MgSO₄). Rotary evaporation of the solvent under reduced pressure produced 2.96 g of a crude yellow oil. The oil was dissolved in a diethyl ether and loaded onto a silica gel column. Elution with diethyl ether/hexane yielded 2.22 g of the titled product as a yellow oil.

Analysis for C₁₅H₂₃OBr (MW=299.26):
•Calcd: C, 60.20 H, 7.75.
Found: C, 60.46; H, 7.87.

EXAMPLE 11

Methyl 7-[4-(hydroxynonyl)phenyl]-5-hydroxy-6heptynoate

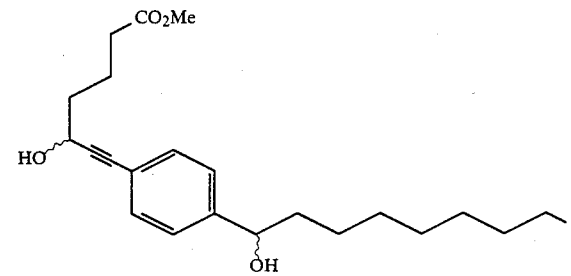

Into a heavy walled Pyrex ® tube was added 102 mg (0.34 mmol) of 1-(p-bromophenyl)-1-nonanol, 53 mg (0.34 mmol) of methyl5-hydroxy-6-heptynoate prepared according to the procedure of Nicolaou et al., J.A.C.S., 106, 2748 (1984), 10 mg (0.009 mmol, 2.5 mole %) of Pd(PPh$_3$)$_4$, and 2 ml (1.4 g) of diisopropylamine. The tube was degassed with argon, sealed and placed in a hot oil bath at approximately 100° C. After about 40 min., a white solid fell out of solution. The reaction was monitored by TLC over the next four hours—some halide was still present, but the acetylene disappeared. The reaction was allowed to cool to R.T. and 40 ml of ether was added. The ether solution was extracted with H$_2$O and brine and then dried (MgSO$_4$). The solvent was stripped from the dried organic phase leaving 100 mg of a yellow oil. The oil was taken up in ether and chromatographed on a silica gel column eluting with 30% diethyl ether/hexane to produce 40 mg of the titled product as a yellow oil.

$^1$H N.M.R. $\delta_{TMS}$ CDCl$_3$ (300 MHz):
7.40
(d, 2H); 7.28(d, 2H); 4.57–4.73(broad m, 2H); 3.69(s, 3H); 2.43(broad t, 2H); 2.12(broad d, 1H); 1.10–1.95(broad m, 19H); 0.88(broad t, 3H).

EXAMPLE 12

Methyl 7[4-(1-hydroxynonyl)phenyl]-5-hydroxy-6Z-heptenoate

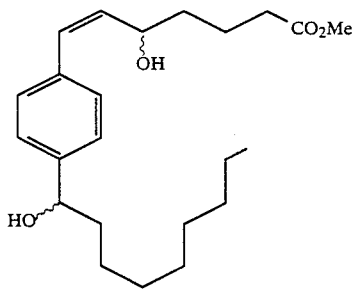

To 2 ml of hexane in a 10 ml round bottom flask was added 38 mg of the titled product of Example 11. The mixture was stirred and benzene was added until the oil went into solution. Upon dissolution, 8 mg of Lindlar catalyst and 0.1 ml of quinoline were added. The flask was evacuated, flushed 5× with H$_2$, and then stirred under a H$_2$ balloon for 3 days. TLC showed that starting material was still present and an additional 8 mg of Lindlar catalyst was added. After 24 hrs. there was almost no starting material remaining. Ether (3 ml) was added to the reaction mixture and it was filtered through Celite ® (diatomaceous earth). The reaction mixture was then sequentially washed with H$_2$O and brine and then dried (MgSO$_4$) Upon removal of the solvent under reduced pressure, the yellow oil residue was chromatographed on a silica gel column slurry packed in 70% diethyl ether/hexane. The titled product was recovered as an oil.

Analysis for C$_{23}$H$_{36}$O$_4$ (MW=376.52):
Calcd: C, 73.36; H, 9.64.
Found: C, 73.10; H, 9.80.
$^1$H N.M.R. $\delta_{TMS}$ CDCl$_3$ (300 MHz):
7.33(d, 2H); 7.25(d, 2H); 6.55(d, 1H); 5.65(dd, 1H); 4.67(broad t, 1H); 4.58(broad t, 1H); 3.67(s, 3H); 2.35(broad t, 2H); 1.20–1.90(broad m, 20H); 0.87(broad t, 3H).

EXAMPLE 13

1-(o-bromophenyl)-1-nonanol

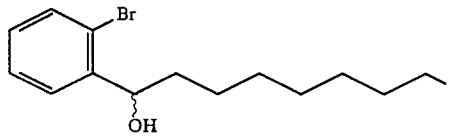

The titled product was prepared according to the procedure of Example 10 substituting o-bromobenzaldehyde for p-bromobenzaldehyde.

EXAMPLE 14

Methyl 7-[2-(1-hydroxynonyl)phenyl]-5-hydroxy-6-heptynoate

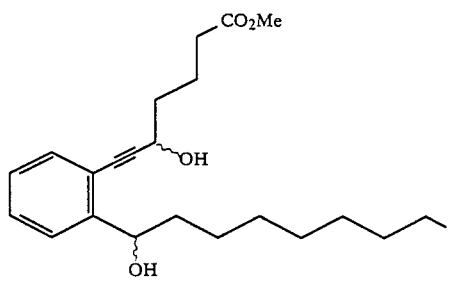

Into a heavy walled Pyrex ® test tube was added 130 mg (0.43 mmol) of 1-(o-bromophenyl)-1-nonanol, 67 mg (0.43 mmol) of methyl 5-hydroxy-6-heptynoate prepared according to the procedure of Nicolaou et al., J.A.C.S., 106, 2748 (1984), 25 mg (0.02 mmol, 5 mole %) of Pd(PPh$_3$)$_4$, and 4 ml (93.0 mg) of diisopropylamine. The reaction was run and worked up according to the procedure of Example 11 to yield 208 mg of a yellow brown oil. The oil was chromatographed on a silica gel column which was eluted with 70% diethyl ether/hexane to produce the titled product as a yellow oil.

$^1$H N.M.R. $\delta_{TMS}$ CDCl$_3$ (300 MHz):
7.18–7.55(m, 4H); 5.12(broad t, 1H); 4.65(m, 1H); 3.69(s, 3H); 2.44(broad t, 2H); 1.1–2.30(broad m, 20H); 0.87(broad t, 3H).

EXAMPLE 15

1-[2-(5-bromo)furanyl]-1-nonanol

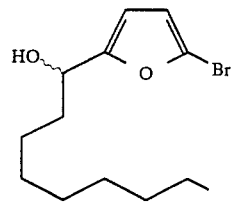

To 0.099 g (4.07 mmol) of pulverized Mg turnings in 5 ml of diethyl ether (in an apparatus set up as in Example 10) was added dropwise with stirring 0.68 g (3.52 mmol) of 1-bromooctane in 10 ml of diethyl ether. After stirring for ½ hour, the reaction mixture was cooled in an ice bath and 20 ml of THF was then added. To the reaction mixture was added dropwise with stirring 0.50 g (2.86 mmol) of 5-bromo-2-furancarboxaldehyde in 20 ml of THF. After the addition was complete, the reaction mixture was stirred for an additional 2 hrs. at R.T. The reaction was quenched with saturated $NH_4Cl$ and the organic layer was sequentially extracted with $H_2O$ and brine and then dried ($MgSO_4$) Upon removal of the solvent by rotary evaporation at reduced pressure, 0.79 g of a brown oil remained. The oil was chromatographed on silica gel, eluting with 25% ethyl acetate/hexane, to yield 0.50 g of the titled product as a yellow oil.

Analysis for $C_3H_{21}O_2Br$ (MW=289.21):
Calcd: C, 53.98; H, 7.32.
Found: C, 54.34; H, 7.17.

EXAMPLE 16

Methyl 7-[-2[5-(1-hydroxynonyl)]furanyl]-5-hydroxy-6-heptynoate

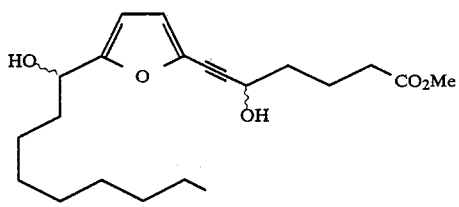

In a heavy walled Pyrex ® test tube containing 3 ml (2.2 g) of diisopropylamine was added 29 mg (0.10 mmol) of the titled product of Example 15, 16 mg (0.10 mmol) of methyl-5-hydroxy-6-heptynoate prepared according to the procedure of Nicolaou et al., J.A.C.S., 106, 1748 (1984), and 9 mg (0.008 mmol, 8 mole %) of $Pd(PPh_3)_4$. The reaction was run and worked up according to the procedure of Example 11 to yield a yellow brown oil. Chromatography of the oil on a silica gel column eluted with 70% diethyl ether/hexane yielded the titled product as a yellow oil. $^1H$ N.M.R. $\delta_{TMD}$ $CDCl_3$ (300 MHz):

6.52(d, 1H); 6.22(d, 1H); 4.63(broad m, 2H);
3.68(s, 3H); 2.35-2.45(broad t, 2H);
1.10-2.13(broad m, 20H); 0.88(broad t, 3H).

EXAMPLE 17

Methyl 7-[-2-[5-(1-hydroxynonyl)]furanyl]-5-hydroxy-6Z-heptenoate

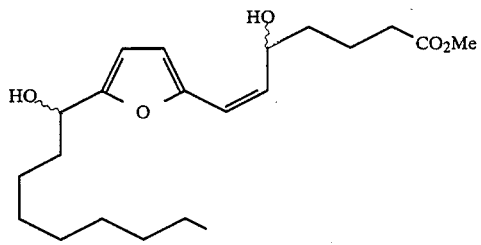

To 16.1 mg (0.044 mmol) of the titled product of Example 16, was added 3 mg of Lindlar catalyst and 15µl of quinoline. The reaction vessel was then flushed 5× with $H_2$ and the reaction mixture was stirred under a $H_2$ balloon for 1 hour. Afterwards, the reaction mixture was worked up as in Example 12 to product a crude yellow oil. The oil was chromatographed on silica gel column which was eluted with 40% ethyl acetate/hexane to yield 13 mg of the titled product as a yellow oil.

$^1H$ N.M.R. $\delta_{TMS}$ $CDCl_3$ (300 MHz):
6.25(s, 2H); 6.15(d, 1H); 5.55(dd, 1H);
5.00(broad t, 1H); 4.65(broad t, 1H); 3.69(s, 3H);
2.40(broad t, 2H); 1.10-1.90(broad m, 20H);
0.87(broad t, 3H).

EXAMPLE 18

1-[2-(5-bromo)thienyl]-1-nonanol

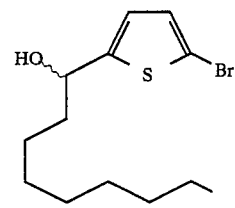

In a 500 ml 3-necked round bottom flask equipped with a condenser and a 250 ml addition funnel was added 1.66 g (68.28 mmol) of Mg. Under a steady flow of arqon, the apparatus was flamed. Upon cooling to R.T., 25 ml of diethyl ether was added to the Mg turnings, followed by the dropwise addition of 12.21 g (63.22 mmol) of 1-bromooctane with vigorous stirring. The Grignard started quickly and addition was continued at a dropwise rate sufficient to maintain steady reflux. After the addition was complete, the reaction was stirred for 1 hr. and 100 ml of freshly distilled THF was added to the Grignard which was then cooled in an ice bath. To the cooled Grignard reagent was added 10.00 (52.34 mmol) of 5-bromo-2-thiophenecarboxaldehyde. The reaction mixture was worked up according to the procedure in Example 10. The resulting brown-yellow oil was chromatographed on a silica gel column. Elution with 20% diethyl ether/hexane produced 9.51 g of the titled product as a yellow oil.

Analysis for $C_{13}H_{21}BrOS$ (MW=305.27):
Calcd: C, 51.14; H, 6.93; Br, 26.18.
Found: C, 51.35: H, 6.94; Br, 26.03.

EXAMPLE 19

Methyl 7-[2-[5-(1-hydroxynonyl)]thienyl]-5-hydroxy-6-heptynoate

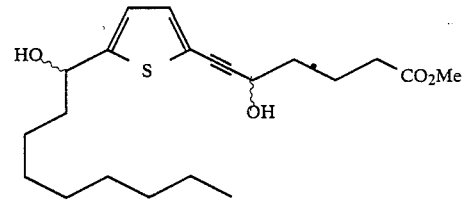

To 30 ml of diisopropylamine in a heavy walled Pyrex ® test tube was added 283 mg (0.93 mmol) of the titled product from Example 18, 143 mg (0.92 mmol) of methyl 5-hydroxy-6-heptynoate prepared according to the procedure of Nicolaou et al., J.A.C.S., 106, 2748 (1984), 43 mg (0.04 mmol, 4 mole %) of $Pd(PPh_3)_4$. The reaction was run and worked up according to the procedure of Example 11. Chromatography of the resulting oil on silica gel column, which was eluted with 75% diethyl ether/hexane, yielded 66 mg of the purified titled product as a yellow oil.

$^1H$ N.M.R. $\delta_{TMS}$ $CDCl_3$ (300 MHz):
7.05(d, 1H); 6.80(d, 1H); 4.85(t, 1H);

4.60(broad t, 1H); 3.68(s, 3H); 2.40(broad t, 2H); 2.15–2.30(m, 2H); 1.70–1.90(m, 6H); 1.20–1.40(m, 12H); 0.88(broad t, 3H).

EXAMPLE 20

Methyl 7-[2-[5-(1-hydroxynonyl)]thienyl]-5-hydroxy-6-heptenoate

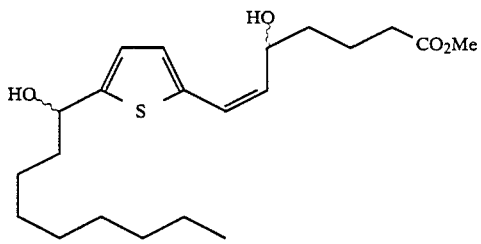

To 42 mg of the titled product of Example 19 was added 4 mg of Lindlar catalyst and 15 μl of quinoline. The reaction vessel was flushed 5× with $H_2$ and then stirred under a $H_2$ balloon overnight. An additional 3 mg of catalyst was added and the reaction stirred as above for an additional 3 hours. The reaction mixture was diluted 10 ml of diethyl ether and filtered through Celite ® (diatomaceous earth). The filtrate was washed with $H_2O$ and brine and then dried ($MgSO_4$). Evaporation of the solvent under reduced pressure produced a crude yellow oil. The oil was chromatographed on a silica gel column, which was eluted with 80% diethyl ether/hexane. The resulting titled product was isolated as a yellow oil.

1H N.M.R. $\delta_{TMS}$ CDCl$_3$ (300 MHz):
6.85(broad s, 2H); 6.53(d, 1H); 5.55(dd, 1H); 4.87(m, 2H); 3.68(s, 3H); 2.38(broad t, 2H); 1.17–2.00(broad m, 20H), 0.87(broad t, 3H).
Analysis for $C_{21}H_{34}O_4S$ (MW=382.55):
Calcd: C, 65.93; H, 8.96.
Found: C, 65.93; H, 9.15.

EXAMPLE 21

7-[4-(1-hydroxynonyl)phenyl]-5-hydroxy-6Z-heptenoic acid, lithium salt

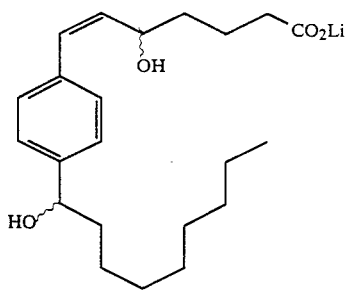

The titled product was prepared according to the reaction described in Example 7 employing the product of Example 12 instead of the product of Example 6. The reaction was run until TLC indicated that all the starting material was consumed.

EXAMPLE 22

7-[2-[5-(1-hydroxynonyl)thienyl]-5-hydroxy-6Z-heptynoic acid, lithium salt

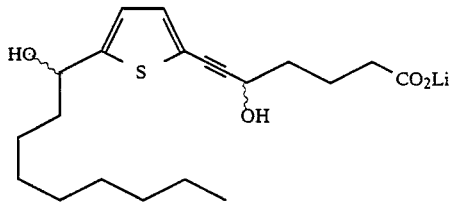

The title product was prepared according to the reaction described in Example 7 employing the product of Example 19 instead of the product of Example 6. The reaction was run until TLC indicated that all the starting material was consumed.

EXAMPLE 23

7-[2-[5-(1-hydroxynonyl)thienyl]-5-hydroxy-6Z-heptenoic acid, lithium salt

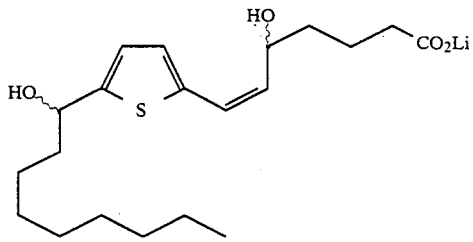

The titled product was prepared according to the reaction described in Example 7 employing the product of Example 20 instead of the product of Example 6. The reaction was run until TLC indicated that all the starting material was consumed.

EXAMPLE 24

1-(5-bromo-2-thienyl)-3-nonyl]oxy](1,1-dimethylethyl)-dimethylsilane

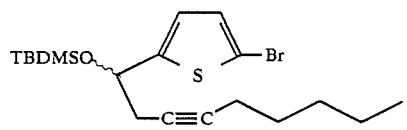

(a) 3-Bromopropyne (48.1 g, 404.3 mmol) in 50 ml of anhydrous ether was added dropwise to Mg turnings (10.8 g, 441.3 mmol) with vigorous stirring. After addition was complete, a few crystals of $HgCl_2$ were added to start the Grignard reaction. The reaction mixture was stirred for 45 min., then cooled in an ice bath and 200 ml of diethyl ether was added. 5-Bromo-2-thiophenecarboxaldehyde (67.4 g, 352.5 mmole) in 75 ml of dry THF was added dropwise at 0° C. The reaction mixture was stirred at 0° C for ½ hour, then warmed to room temperature and stirred overnight over argon. The reaction was quenched with 100 ml of saturated ammonium chloride. The organic layer was washed with 2×150 ml of brine, then dried over sodium sulfate to yield 42.72 g of a red oil. The oil was chromatographed on silica gel using 10% methyl t-butyl ether/90% 1,1,2-trichlorotrifluoroethane as eluant. The product, 1-(5-bromothienyl)-1-(hydroxy)-3-butyne was isolated as a yellow oil and is represented by the formula

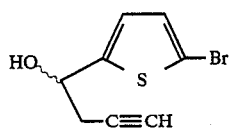

(b) The product of Example 24 (4.63 g, 20.03 mmol) in 20 ml of dry DMF was added to a 100 ml round bottomed flask. The solution was cooled in an ice bath and imidazole (3.00 g, 44.06 mmol) was added all at once. After the solid had dissolved, t-butyldimethylchlorosilane (3.32 g, 22.03 mmol) was added in one portion. The solution was stirred in the ice bath under argon for 10 min., then stirred at room temperature for 2 hours. TLC in toluene showed no starting material. The reaction mixture was poured into 400 ml of diethyl ether and a yellow gel formed. About 20 ml of water was added. The layers were separated, and the organic layer was washed 3× with 75 ml of water, 1× with 75 ml brine, dried over magnesium sulfate. The solvent was removed under vacuum to give a yellow oil. Chromatography of the yellow oil on a silica gel column packed in 10% ether/hexane gave 6.48 g of the product, [[1-(5-bromo-2-thienyl)-3-butynyl]oxy](1,1-dimethylethyl)dimethylsilane, as a yellow oil. The product is represented by the formula

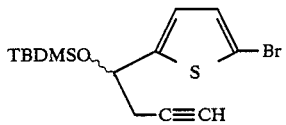

(c) A 1.6 M solution of n-butyl lithium in hexane (0.22 ml, 0.35 mmole) was added to a solution of diisopropylamine (0.06 ml, 0.43 mmol) in THF at 0° C. The mixture was stirred for ½ hour at 0° C., then cooled to −78° C. The product from Example 24(b) (0.1 g , 0.29 mmol) in 1.0 ml of THF was added over a 1 minute period. The reaction mixture was stirred 5 minutes at −78° C., then warmed to −20° C. and stirred at −20° C. for ½ hour. 1-Iodopentane (0.1 ml, 0.75 mmole) was added, followed by 0.5 ml of hexamethyl phosphoric triamide (HMPA). The reaction was allowed to warm to room temperature and was stirred at room temperature overnight. The reaction mixture was quenched with water. The reaction mixture was poured into hexane and then extracted 4× with water and 1× with brine, then dried over magnesium sulfate. Removal of the solvent gave the title compound as a red oil.

EXAMPLE 25

Methyl 7-[5-[1-[[(1,1-dimethylethyl)dimethylsilyl]oxy]-3-nonynyl]-2-thienyl]-5-hydroxy-6-heptynoate

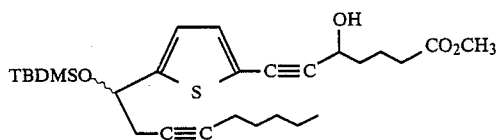

[[1-(5-bromo-2-thienyl)-3-nonyl]oxy](1,1-dimethylethyl)dimethylsilane (145 mg, 0.35 mmol), and methyl 5-hydroxy-6-heptynoate (60 mg, 0.38 mmol) were dissolved in distilled diisopropylamine (10 ml) containing Pd(PPh₃)₄ (25 mg). The mixture was heated at 100° C. in a heavy walled Pyrex ® tube for 2 hrs. The mixture was cooled and partitioned between ether and water. The organic layer was washed with brine, dried over sodium sulfate, evaporated in vacuo and the residue purified by chromatography on silica gel (ethyl acetate/hexane 2:8). The product was obtained as a yellow oil, 40 mgs.

Microanalysis: Calculated: C, 66.07, H, 8.63.
Found: C, 66.27, H, 8.98.

EXAMPLE 26

Methyl 7-[5-[1-[[(1,1-dimethylethyl)dimethylsilyl]oxy]-3-nonenyl]-2-thienyl]-5-hydroxy-6-heptenoate

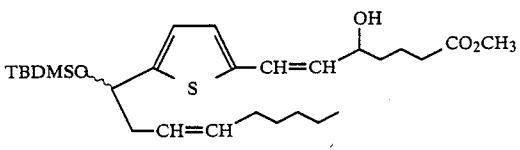

The product of Example 25 (25 mg, 0.05 mmol) was dissolved in hexane (2 ml), containing Lindlar catalyst (10 mg) and quinoline (1 drop). The mixture was evacuated, flushed with hydrogen and then stirred under a hydrogen atmosphere for 24 hrs. The reaction mixture was filtered through Celite ® filter agent, evaporated in vacuo and the residue purified by chromatography on silica gel (ethyl acetate/hexane 1.5:8.5).

The title compound was obtained as a yellow oil along with 14.4 mg of methyl [5-[1-[[(1,1-dimethylethyl)dimethylsilyl]oxy]-3-nonenyl]-6-hydroxy-2-thiopheneheptanoate represented by the following formula.

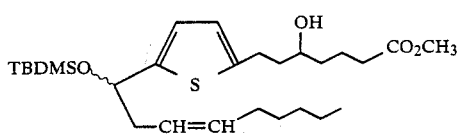

EXAMPLE 27

5-hydroxy-7-[5-(1-hydroxy-3-nonenyl)-2-thienyl]-6-heptenoic acid

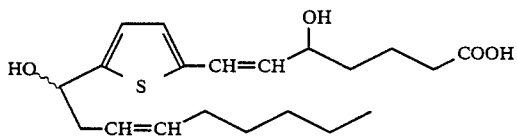

(a) Methyl 7-[5-[1-[[(1,1-dimethylethyl)dimethylsilyl]oxy]-3-nonenyl-2-thienyl]-5-hydroxy-6-heptenoate (20mg) was dissolved in dry THF (1 ml) containing 5 equivalents of a 1 M solution of tetrabutylammonium fluoride in THF. The mixture was stirred until all starting material had disappeared and then partitioned between ethyl acetate and water. The solvent was dried over sodium sulfate and evaporated to afford a crude residue which was purified by radial band chromatography to afford 2 mg of the title compound.

(b) Treatment of the acid prepared in Example 27a with 1 equivalent of an ethereal solution of diazomethane gives the methyl ester.

What is claimed is:

1. A compound comprising 5-hydroxy-7-[5-(1-hydroxy-3-nonenyl)-2-thienyl]-6-heptenoic acid.

2. A pharmaceutical composition according to claim 1 wherein said compound is 5-hydroxy-7-[5-(1-hydroxy-3-nonenyl)-2-thienyl]-6-heptenoic acid.

3. A method of treating an inflammatory condition in mammals comprising administering a non toxic therapeutic effective amount of a compoound according to claim 1 to a mammal in need of such treatment.

* * * * *

UNITED STATES PATENT AND TRADEMARK OFFICE
CERTIFICATE OF CORRECTION

PATENT NO. : 4,895,869

Page 1 of 3

DATED : January 23, 1990

INVENTOR(S) : Djuric, et al.

It is certified that error appears in the above-identified patent and that said Letters Patent is hereby corrected as shown below:

On the title page of the patent, in the section in which the assignee is designated, reading "C. D. Searle & Co." should read -- G. D. Searle & Co. --.
Column 2, line 34, reading "lower alkyl 1-6 carbon atoms" should read
-- lower alkyl having 1-6 carbon atoms --.
Column 4, lines 41-42, reading "approximately" should read
-- approximately 5μM --.
Column 6, line 50, reading "about 200" should read -- about 2.0 --.
Column 6, line 64, reading "(ıllı )" should read -- (|||·· ) --.
Column 7, Table 1, the first structure, that portion of the structure reading  should read 

Column 10, line 34, reading "4.72(t, $^1_1$H)" should read -- 4.72(t, 1H) --.
Column 10, line 68, reading "4.74(t, $^1$H" should read -- 4.74(t, 1H) --.
Column 11, line 7, reading "(t-butyldimethylsilkoxy)" should read
-- (t-butyldimethylsiloxy) --.
Column 11, the first structure, that portion of the structure reading
 should read 

Column 11, line 46, reading "6.44(d, $^1$H)" should read -- 6.44(d, 1H) --.
Column 11, the last structure, that portion of the structure reading
 should read 

Column 12, line 2, reading "-ethyleneyl]-" should read -- -ethenyl1- --.
Column 12, the first structure, that portion of the structure reading
 should read 

Column 12, lines 50-51, reading "-hydroxy6Z-" should read -- -hydroxy-6Z- --.

UNITED STATES PATENT AND TRADEMARK OFFICE
CERTIFICATE OF CORRECTION

PATENT NO. : 4,895,869

DATED : January 23, 1990

INVENTOR(S) : Djuric, et al.

It is certified that error appears in the above-identified patent and that said Letters Patent is hereby corrected as shown below:

Column 12, the last structure, that portion of the structure reading  should read 

Column 13, line 10, reading "$\delta_{d4\ Na-TSP}$" should read -- $\delta_{d4}Na\text{-}TSP$ --.

Column 14, line 3, reading "al" should read -- all --.

Column 14, line 55, reading "-6heptynoate" should read -- -6-heptynoate --.

Column 15, line 3, reading "methyl5-hydroxy-" should read --methyl 5-hydroxy- --.

Column 15, lines 21-22, reading
"7.40
(d, 2H" should read -- 7.40(d, 2H) --.

Column 15, line 28, reading "7[4-(1-" should read -- 7-[4-(1- --.

Column 17, line 11, reading "$C_3H_{21}O_2Br$" should read -- $C_{13}H_{21}O_2Br$ --.

Column 17, line 16, reading "7-[-2[" should read -- 7-[2-[ --.

Column 17, line 39, reading "$\delta_{TMD}$" should read -- $\delta_{TMS}$ --.

Column 17, line 46, reading "7-[-2-[" should read -- 7-[2-[ --.

Column 19, line 37, reading "1H" should read -- $^1H$ --.

Column 20, line 43, reading "1-(5-bromo-" should read -- [[1-(5-bromo- --.

Column 22, line 58, reading "-6-hydroxy-" should read -- -$\delta$-hydroxy- --.

UNITED STATES PATENT AND TRADEMARK OFFICE
CERTIFICATE OF CORRECTION

PATENT NO. : 4,895,869

DATED : January 23, 1990

INVENTOR(S) : Djuric, et al.

It is certified that error appears in the above-identified patent and that said Letters Patent is hereby corrected as shown below:

Column 24, Claim 2, lines 11-13, reading "A pharmaceutical composition according to claim 1 wherein said compound is 5-hydroxy-7-[5-(1-hydroxy-3-nonenyl)-2-thienyl]-6-heptenoic acid." should read -- A pharmaceutical composition comprising the compound of claim 1 and a non-toxic pharmaceutically acceptable carrier. --.

Signed and Sealed this

Seventeenth Day of March, 1992

Attest:

HARRY F. MANBECK, JR.

Attesting Officer     Commissioner of Patents and Trademarks